United States Patent
Ettlin (10) Patent No.: US 9,919,310 B2
(45) Date of Patent: Mar. 20, 2018

(54) APPARATUS FOR ANALYZING A TEST LIQUID

(71) Applicant: SULZER MIXPAC AG, Haag (CH)

(72) Inventor: Josef Ettlin, Eichberg (CH)

(73) Assignee: SULZER MIXPAC AG, Haag (CH)

( * ) Notice: Subject to any disclaimer, the term of this patent is extended or adjusted under 35 U.S.C. 154(b) by 0 days.

(21) Appl. No.: 14/766,990

(22) PCT Filed: Feb. 10, 2014

(86) PCT No.: PCT/EP2014/052561
§ 371 (c)(1),
(2) Date: Aug. 11, 2015

(87) PCT Pub. No.: WO2014/124903
PCT Pub. Date: Aug. 21, 2014

(65) Prior Publication Data
US 2015/0367343 A1    Dec. 24, 2015

(30) Foreign Application Priority Data

Feb. 12, 2013  (EP) .................................... 13154868

(51) Int. Cl.
*B01L 3/00*  (2006.01)
*A61B 10/00*  (2006.01)

(52) U.S. Cl.
CPC ........ *B01L 3/5023* (2013.01); *A61B 10/0045* (2013.01); *B01L 3/5029* (2013.01); *A61B 10/007* (2013.01); *A61B 10/0051* (2013.01); *B01L 2200/10* (2013.01); *B01L 2300/0609* (2013.01); *B01L 2300/069* (2013.01);
(Continued)

(58) Field of Classification Search
CPC ............ A61B 10/0045; A61B 10/0051; A61B 10/007; B01L 2200/10; B01L 2300/0609; B01L 2300/0663; B01L 2300/0672; B01L 2300/069; B01L 2400/0475; B01L 2400/0478; B01L 2400/049; B01L 3/5023; B01L 3/5029
See application file for complete search history.

(56) References Cited

U.S. PATENT DOCUMENTS 5,785,044 A    7/1998  Meador et al.
9,670,528 B2 *  6/2017  Handique ............ C12Q 1/6806
(Continued)

FOREIGN PATENT DOCUMENTS

DE    2711201 A1    9/1978
DE    69707925 T2    6/2002
(Continued)

*Primary Examiner* — Sally A Merkling
(74) *Attorney, Agent, or Firm* — Global IP Counselors, LLP (57) ABSTRACT

An apparatus for analyzing a test liquid includes an inlet chamber, a preparation chamber and an analysis element. The inlet chamber receives the test liquid. Test liquid is configured to be brought from the inlet chamber via the preparation chamber onto the analysis element. A volume of the preparation chamber is capable of being increased, the test liquid being sucked into the preparation chamber from the inlet chamber due to an increase of the volume of the preparation chamber. A fixed quantity of test liquid is thus sucked into the preparation chamber, which enables precise analysis results possible.

15 Claims, 4 Drawing Sheets

(52) U.S. Cl.
CPC ............... *B01L 2300/0663* (2013.01); *B01L 2300/0672* (2013.01); *B01L 2400/049* (2013.01); *B01L 2400/0475* (2013.01); *B01L 2400/0478* (2013.01)

(56) References Cited

U.S. PATENT DOCUMENTS

| | | | |
|---|---|---|---|
| 2003/0064526 A1 | 4/2003 | Niedbala et al. | |
| 2006/0292034 A1* | 12/2006 | Gould | A61B 10/0051 422/400 |
| 2009/0019953 A1* | 1/2009 | Bommarito | B01L 3/5029 73/863.71 |
| 2011/0127294 A1* | 6/2011 | Pearcy | A61J 1/2089 422/501 |

FOREIGN PATENT DOCUMENTS

| | | |
|---|---|---|
| DE | 202008017883 U1 | 11/2010 |
| WO | 98/42821 A1 | 10/1998 |
| WO | 2011/018658 A1 | 2/2011 |

\* cited by examiner

APPARATUS FOR ANALYZING A TEST LIQUID

CROSS-REFERENCE TO RELATED APPLICATIONS

This application is a U.S. National stage application of International Application No. PCT/EP2014/052561, filed Feb. 10, 2014, which claims priority to EP Application No. 13154868.7 filed on Feb. 12, 2013, the contents of each of which is hereby incorporated herein by reference.

BACKGROUND

Field of Invention

The invention relates to an apparatus for analyzing a test liquid.

Background Information

Such apparatus can be used, for example, for analyzing saliva or urine of a test person. It is, however, also possible that other liquids are analyzed or a sample substance to be analyzed, for example in the form of a solid, is first mixed with a so-called washing-out liquid or is dissolved therein and the test liquid obtained in so doing is subsequently analyzed. The analysis can be used, for example, for the detection of drugs, explosives or other substances such as traces of nuts.

In such analyses, the sample substance, for example in the form of saliva, is first mixed with the washing-out liquid so that a test liquid arises which can be analyzed. The mixture is in particular achieved such that a sample collector with which the sample substance can be received is washed out in the washing-out liquid. The test liquid is subsequently usually prepared. For this purpose, the test liquid can be brought into connection with a reaction partner, for example in the form of gold conjugate. The preparation is also called a so-called incubation. After a fixed waiting period, the test liquid thus prepared is conducted to an analysis element which, for example, contains a test strip which is also called a so-called lateral flow assay. The test strip is acted on at one end by a test liquid which then flows through the test strip and collects in a collection path at the oppositely disposed end of the test strip. The test strip can have a nitrocellulose membrane on which test lines and control lines are arranged which react with the test liquid and on which a reaction and thus the analysis result can be read off. The analysis result can, for example, be read of by means of a special electronic evaluation apparatus and processed.

An apparatus for analyzing a test liquid is described in US 2006/ 0292034 A1. The apparatus has an inlet chamber, a preparation chamber and an analysis element having a test strip. The test liquid in the form of saliva of a test person can be received by a sample collector and introduced into the inlet chamber. The sample collector is in this respect pressed out so that test liquid enters into the inlet chamber. The inlet chamber is displaced in the direction of the preparation chamber arranged beneath it by pressing the sample collector onto the base of the inlet chamber, whereby a volume of the preparation chamber is reduced in size and thus varied. The inlet chamber is displaced so far until the base of the inlet chamber tears and thus a not precisely defined quantity of the test liquid flows from the inlet chamber into the preparation chamber. After a fixed incubation time of approximately 2-3 minutes, a slider arranged between the preparation chamber and the test strip is opened so that the prepared test liquid can move onto an end of the test strip. After a reaction time, the analysis result can be read off on the test strip as described above.

An apparatus for analyzing a test liquid is likewise described in DE 202008 017 883 U1. The apparatus has a preparation chamber in the form of a mixing chamber and an analysis element having a test strip. On the utilization of the apparatus, test liquid is filled from a separate washing-out apparatus into the preparation chamber from where it is conducted onto the test strip after the preparation. So that a specific quantity of test liquid is filled into the preparation chamber, it has a filling level marking up to which a user of the apparatus should fill in test liquid. A monitoring or checking of the actually filled-in quantity of test liquid is not possible.

Against this background, it is the object of the invention to propose an apparatus for analyzing a test liquid which is simple and reliable to handle. This object is satisfied in accordance with the invention by an apparatus for analyzing a test liquid having the features recited herein.

The apparatus in accordance with the invention for analyzing a test liquid has an inlet chamber, a preparation chamber and an analysis element. The inlet chamber is provided to receive the test liquid. Test liquid can be brought from the inlet chamber via the preparation chamber onto the analysis element and a volume of the preparation chamber is variable.

In accordance with the invention, the volume of the preparation chamber can be increased, with test liquid being sucked out of the inlet chamber into the preparation chamber by an increase of the volume of the preparation chamber. On the increasing of the volume of the preparation chamber, a vacuum is generated in the preparation chamber on the basis of which an exactly fixed quantity of test liquid is sucked into the preparation chamber. The sucked-in quantity in this respect corresponds to the volume variation of the preparation chamber. It can thus simply be ensured that a defined quantity of test liquid moves into the preparation chamber, which ensures a defined preparation and thus an exact analysis result. The user of the apparatus is in particular assisted in this respect in increasing the volume of the preparation chamber by exactly a defined degree. For this purpose, for example, a mechanical abutment can be provided which bounds the volume increase or a latching or fixing of a starting position and a preparation position of an actuation element by means of which the volume increase can be carried out.

In this respect the connection between the inlet chamber and the preparation chamber is in particular not always present, but it can rather be interrupted. The connection in particular also only exists then when test liquid should actually be introduced into the preparation chamber. In this way it is, on the one hand, prevented that test liquid moves into the preparation chamber in an unwanted manner in a starting position and, on the other hand, it is prevented that further test liquid can move into the preparation chamber during or after the preparation and can thus influence the analysis result. In this way very exact analyses are made possible.

The analysis element in particular has one or more test strips.

In an embodiment of the invention, in a starting state of the apparatus, a washing out liquid is arranged in the inlet chamber and produces the test liquid when mixed with a sample substance. A starting state of the apparatus is to be understood as an unused state, that is the state before the start of an analysis of a sample substance or of a test liquid. The sample substance can, for example, be designed as a liquid, a solid or any desired mixture of liquid and solid. Examples for sample substances are saliva, urine, blood, swabs from objects or food samples. A separate container for the washing-out liquid, which would have to be separately packed and supplied, can be dispensed with by the provision of washing-out liquid in the inlet chamber. In addition, the handling is particularly easy for the user since he does not have to handle a plurality of containers.

The apparatus in accordance with the invention can have a cover by means of which the inlet chamber can be closed. It is also possible that, in the starting state, a sample collector is arranged at least partly in the inlet chamber and can close the inlet chamber so that no washing-out liquid can exit. It is also possible that an envelope for the sample collector is provided in which the sample collector is stored in the starting state. The named envelope is then in particular designed such that it can be partly arranged in the inlet chamber and thus closes it. The envelope can then also serve to close the inlet chamber after the washing-out of the sample collector and thus prevent an exiting of washing-out liquid or test liquid.

In an embodiment of the invention, the apparatus has a housing with an inner housing space. A preparation element is partly or completely arranged within the inner housing space and bounds the preparation chamber partly or completely. The preparation element can also bound two separate preparation chambers. An inlet element is likewise partly or completely arranged within the inner housing space and bounds the inlet chamber partly or completely. The preparation element and the inlet element are arranged behind one another in an axial direction and are connected to one another so that a displacement of the inlet element in the axial direction away from the preparation element increases the volume of the preparation chamber. A compact design of the apparatus is thus made possible. Since the inlet chamber anyway has to be accessible from outside the housing to introduce the sample substance, the volume of the preparation chamber can be increased by the described design of the apparatus without it itself having to be accessible from outside the housing.

The inlet element and the preparation element in particular each have a hollow cylindrical basic shape so that the named axial direction corresponds to the axial direction of the inlet element and of the preparation element. Diameters of the inlet element and of the preparation element in particular differ from one another so that the corresponding inner housing space is predominantly composed of cylinders with different diameters. The diameter of the preparation element is in particular larger than the diameter of the inlet element so that the housing has an abutment which bounds the axial extent of the preparation element and thus the increase of the volume of the preparation chamber and thus the increase of the volume of the preparation chamber by a defined degree is made possible.

The coupling of the preparation element to the inlet element in particular takes place via a peripheral, inwardly directed groove of the preparation element and a corresponding collar of the inlet element. The arrangement of groove and collar can also be reversed.

The preparation element can in particular have peripheral folds which are pulled apart for increasing the volume of the preparation chamber and thus allow the volume increase. Alternatively or additionally, the preparation element can be composed of an elastic material such as an elastomer or silicone.

So that the preparation element is not also completely displaced on a displacement of the inlet element in a direction directed away from the preparation chamber, a fixing of the inlet element in the axial direction with respect to the housing is necessary. This can be realized, for example, by a peripheral collar at an end of the preparation element which is disposed opposite the preparation element and which contacts a corresponding edge of the housing.

In an embodiment of the invention, the inlet element has an actuation element which is arranged outside the housing. The actuation element is designed so that a force for displacing the inlet element can be introduced via the actuation element. The inlet element can thus easily be displaced and test liquid can thus be sucked into the preparation chamber.

The inlet element and the actuation element are in particular made in one piece. It is, however, also possible that they are designed as separate parts which are suitably connected to one another. The actuation element in particular has the same outer contour as the housing and adjoins the housing in the axial direction.

The actuation element can be displaced or in particular rotated in the axial direction to displace the inlet element with respect to the housing. To convert the rotary movement into an axial movement, that is a displacement of the inlet element, the inlet element has a first thread and the housing has a corresponding second thread. A particularly simple handling of the apparatus is thus possible.

In this respect, the inlet element can have an external thread and the housing can have an internal thread or vice versa. The apparatus can, for example, be configured so that a rotation of the actuation element by 180° with respect to the housing displaces the inlet element so far that the preparation element abuts the abutment of the housing and thus the intended quantity of test liquid is sucked out of the inlet chamber into the preparation chamber.

In an embodiment of the invention, the inlet element can be rotated with respect to the housing from a starting position into a preparation position for increasing the volume of the preparation chamber. There is only a connection between the inlet chamber and the preparation chamber between the starting position and the preparation position. There is thus no connection between the inlet chamber and the preparation chamber in the two named positions. It is thus prevented, on the one hand, that test liquid can unintentionally move into the preparation chamber in the starting position and, on the other hand, it is prevented that even further fluid can continue to flow during or after the preparation and can thus influence the analysis result. Very exact analyses thus become possible.

For this purpose, the inlet element, for example, has one or more passages in the direction of the preparation element. The preparation element has corresponding passages or holes which are arranged so that they are only flush with the passages of the inlet element between the starting position and the preparation position.

In an embodiment of the invention, a film which separates the separation chamber from the analysis element in the intact state is arranged between the preparation chamber and the analysis element. To start the analysis of the test liquid, the film can be pierced by means of a punch so that prepared test liquid can flow from the preparation chamber to the analysis element. A simple and inexpensive design of the apparatus and a simple handling are thus made possible.

The analysis element in particular has the named punch and is pivotably connected to the housing. It can adopt a position of rest and an indication position with respect to the housing, with it being configured and arranged such that, on a pivoting with respect to the housing, the punch of the analysis element pierces the film arranged between the preparation chamber and the analysis element and the analysis of the test liquid is thus started. The analysis procedure can thus be started very simply by pivoting the analysis element.

The analysis element in this respect in particular has a predominantly parallelepiped-shaped basic shape. In the position of rest, a main direction of extent of the analysis element is arranged predominantly parallel to the axial direction. To bring it into the indication position, it is, for example, pivoted or unfolded by 90° with respect to the housing. The analysis element usually contains one or more test strips to whose shape it is matched. In this case, the named main direction of extent extends in the direction of flow of the test strip. The analysis element is in the described position of rest in the starting state of the apparatus. The apparatus is thus very compact in the starting state, in which it is also stored and sold, and is thus simple and inexpensive to store and to transport. The analysis element is in particular arranged so that openings for reading the analysis result are oriented toward the housing in the position of rest and are thus protected.

The pivotable arrangement of the analysis element with respect to the housing is independent of the manner how test liquid is brought from the inlet chamber into the preparation chamber. The described arrangement can thus also be combined with any other possible manner of bringing test liquid from the inlet chamber into the preparation chamber.

In an embodiment of the invention, the apparatus has a housing which has the inlet chamber, an inner housing space, an inflow line from the inlet chamber to the inner housing space and an outflow line from the inner housing space to the analysis element. A plunger with a step is displaceably arranged in the inner housing space. In addition, a ring piston is arranged on the plunger and can be displaced at least piece-wise both in the inner housing space and with respect to the plunger. The preparation chamber is in this case formed by an end face of the named step of the plunger facing the ring piston, by the inner housing space and by the ring piston. The plunger and the ring piston are in this respect configured and arranged such that, on a displacement of the plunger from a starting position into a preparation position, the ring piston first remains stationary with respect to the inner housing space and thus the volume of the preparation chamber is increased. It is not necessary in this respect that the ring piston does not move at all. A small displacement of the ring piston is permitted; however it must be considerably smaller than the displacement of the plunger. This allows a simple design of the apparatus.

So that the ring piston first remains stationary, the individual parts can, for example, be designed such that the friction between the ring piston and the inner housing space is larger than the friction between the ring piston and the plunger. Additionally or alternatively, the inner housing space can have a step which first holds the ring piston in its position. The inner housing space in particular has a predominantly cylindrical shape. Its axis extends in this respect in particular parallel to the main direction of extent of the analysis element. This allows a particularly compact design of the apparatus.

In an embodiment of the invention, the plunger and the ring piston are configured and arranged such that, in the starting position, the inflow line from the inlet chamber is closed toward the inner housing space. There is thus no connection between the inlet chamber and the preparation chamber in the starting position. It is thus prevented that test liquid unintentionally flows into the preparation chamber in the starting position. The inflow line is in this respect in particular closed by the plunger which has a corresponding shape for this purpose and can additionally have sealing elements such as 0 rings.

The outflow line from the inner housing space to the analysis element is in particular closed in the preparation position. It is thus prevented that the test liquid already moves to the analysis element before the end of the preparation. For this purpose, in particular the plunger is also used, with the named or additional sealing elements likewise being able to act.

In an embodiment of the invention, the plunger has a driver which is configured such that it bounds a relative movement between the plunger and the ring piston. The driver is, for example, configured as a region having a larger diameter than the passage of the ring piston. The plunger and the ring piston are arranged in the preparation position such that the inflow line from the inlet chamber to the inner housing space is closed. It is thus prevented that further test liquid can still continue to flow during or after the preparation and can thus influence the analysis result. This is in particular implemented in that the ring piston is taken on so far by the driver, starting from its position in the starting position, that it closes the inflow line. For better sealing, the ring piston can have peripheral sealing lips or additional sealing elements, for example in the form of 0 rings.

In addition, the plunger and the ring piston can adopt an analysis position in which the outflow line from the inner housing space to the analysis element is open and a connection from the inlet chamber to the preparation chamber is interrupted. It is thus made possible that prepared test liquid can move to the analysis element and simultaneously prevents that in so doing still further, untreated, test fluid flows into the preparation chamber. The named connection from the inlet chamber to the preparation chamber is in this respect in particular interrupted by the ring piston and the plunger. It can be possible in this respect that the inflow line from the inlet chamber to the inner housing space is admittedly open, but no test fluid can move from the inflow line into the preparation chamber.

In an embodiment of the invention, the apparatus has an actuation element which is arranged displaceable with respect to the housing, which is coupled to the plunger and by means of which a force can be introduced for displacing the plunger. A simple handling of the apparatus is thus made possible. It is possible that latches are provided between the housing and the actuation element for the secure setting of the different positions, said latches fixing the actuation element in the individual positions, but being able to be overcome by pressing. For this purpose, the actuation element can have one or more cut-outs and the housing can have correspondingly positioned elevated portions.

The actuation element can in particular have one or more cut-outs through which markings are visible which indicate a current position of the inlet element or of the plunger. In addition, information can also be given on corresponding waiting times at the individual positions. A user can thus be informed simply over the current progress of the analysis and his attention can be drawn to possible waiting times which have to be observed. A secure handling and thus also reliable analysis results are thus achieved.

In an embodiment of the invention, the housing has a storage space for a sample collector. All the parts required for the analysis of the test substance can thus be combined together, which allows a simple handling. As already stated, the inlet chamber can serve as a storage space. It is, however, also possible that an additional storage space is provided.

The individual parts of the apparatus can, for example, be composed of polyethylene or polypropylene and in particular be manufactured by means of an injection molding process.

Further advantages, features and details of the invention result with reference to the following description of embodiments and with reference to drawings in which elements which are the same or have the same function are provided with identical reference numerals.

BRIEF DESCRIPTION OF THE DRAWINGS

Referring now to the attached drawings which form a part of this original disclosure.

DETAILED DESCRIPTION OF THE EMBODIMENTS

Figures 1, 2:
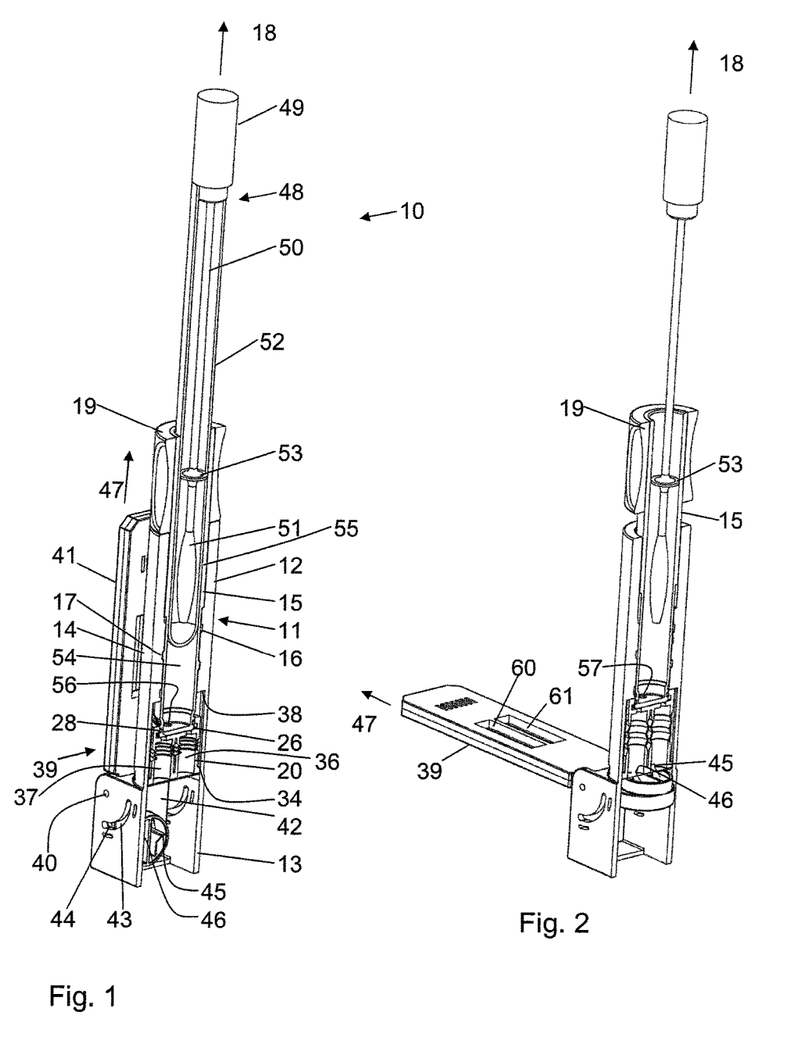
FIG. 1 is an apparatus for analyzing a test liquid in a starting state.
FIG. 2 is the apparatus from FIG. 1 in an analysis position.

In accordance with FIG. 1, an apparatus 10 for analyzing a test liquid has a housing 11 which is composed of a predominantly cylindrical section 12 and a parallelepiped-shaped section 13 downwardly adjoining it. The cylindrical section 12 of the housing 11 in this respect forms an inner housing space 55. The parallelepiped-shaped section 13 is configured so that the apparatus 10 can be placed on a planar surface such that the cylindrical section 12 faces perpendicularly upward. A predominantly cylindrical inlet element 15 is arranged within the cylindrical section 12 of the housing 11 in an upper region 14 such that a part of the inlet element 15 projects out of the cylindrical section 12 of the housing 11. The inlet element 15 bounds an inlet chamber 54. The cylindrical section 12 of the housing 11 has an internal thread 16 and the inlet element 15 has a corresponding external thread 17. The inlet element 15 can thus be pushed further out of the cylindrical section 12 of the housing 11 in the axial direction 18 of the cylindrical section 12 of the housing 11 by rotating the inlet element 15 with respect to the cylindrical section 12 of the housing 11. To be able to introduce a force for rotating and thus displacing the inlet element 15, an actuation element 19 is rotationally fixedly arranged at the part of the inlet element 15 which projects out of the cylindrical section 12 of the housing 11. The actuation element 19 has a hollow cylindrical basic shape which adapts to the shape of the cylindrical section 12 of the housing 11. To be able to grip the actuation element 19 better, it has a total of four indentations distributed at its periphery.

Figure 3:
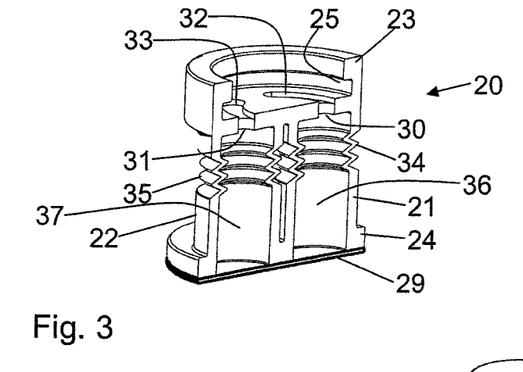
FIG. 3 is a preparation element of the apparatus of FIG. 1.

A preparation element 20, which is shown in more detail in FIG. 3, adjoins the inlet element 15 in the direction of the parallelepiped-shaped section 13 of the housing 11. The preparation element 20 has two predominantly cylindrical center parts 21, 22 which are arranged in parallel with one another and coaxially to the axial direction 18. The center parts 21, 22 each have peripheral folds 34, 35 which can be pulled apart. The center parts 21, 22 are connected via a connection collar 23 in the direction of the actuation element 19 and via an end collar 24 in the direction of the parallelepiped-shaped section 13 of the housing 11. The connection collar 23 has a cylindrical outer contour which is adapted to the inner contour of the cylindrical section 12 of the housing 11. It moreover has an inwardly peripheral groove 25 into which a corresponding collar 26 of the inlet element 15 engages so that, on a displacement of the inlet element 15 in the axial direction 18, the connection collar 23 of the inlet element 20 is taken along. In addition, a sealing element 28 in the form of an 0 ring is arranged between the inlet element 15 and the connection collar 23 of the preparation element 20. The end collar 24 likewise has a cylindrical outer contour which is adapted to the inner contour of the cylindrical section 12 of the housing 11. It is closed by a film 29 in the direction of the parallelepiped-shaped section 13 of the housing 11. In the installed state, the end collar 24 contacts an edge 34 of the cylindrical section 12 of the housing 11 so that it cannot be displaced in the direction of the actuation element 19. Only the connection collar 23 of the preparation element 20 is thus taken along on a displacement of the inlet element 15 in the axial direction 18 and the end collar 24 remains stationary. The folds 34, 35 of the center parts 21, 22 are pulled part in this process. The cylindrical section 12 of the housing 11 has an abutment 38 which the connection collar 24 abuts after a defined displacement path so that the displacement of the connection collar 24 is limited. The threads 16, 2, the abutment 38 and the installation position of the preparation element 20 are thus coordinated with one another so that, starting from a starting position of the actuation element 19, and thus of the inlet element 15, the connection collar 23 abuts the abutment 38 after a rotation of the actuation element 19 by 180° with respect to the housing 11 so that a preparation position is reached.

The center parts 21, 22 are closed in the direction of the connection collar 23, except for a circular hole 30, 31. The center parts 21, 22 of the preparation element 20 thus form two mutually separate preparation chambers 36, 37 whose volume can, as described, be increased by a defined degree. The holes 30, 31 are connected to respective arcuate inflow 32, 33 which are open in the direction of the connection collar 23 and are closed in the direction of the end collar 24. The purpose of the inflows 32, 33 will be explained in more detail further below.

An analysis element 39 is pivotably arranged at the parallelepiped-shaped section 13 of the housing 11. The analysis element 39 has a predominantly parallelepiped-shaped basic shape with a main direction of extent 47. It contains two test strips, not shown in more detail, which are arranged so that their direction of flow extends in the direction of the main direction of extent 47. The test strips are partly visible via two cut-outs 60, 61 of the analysis element 39.

In the starting state of the apparatus 10 shown in FIG. 1, and thus in a position of rest of the analysis element 39, the analysis element 39 is arranged parallel to the axial direction 18 so that the main direction of extent 47 extends parallel to the axial direction 18. The cut-outs 60, 61 via which the test strips are visible are oriented toward the housing 11 in this state. The analysis element 39 is pivotable about an axis 40, with a first part 41 of the analysis element 39 pivoting away from the cylindrical section 12 of the housing 10 and a second part 42 pivoting into the parallelepiped-shaped section 13 of the housing 11. The parallelepiped-shaped section 13 of the housing 11 has an arcuate cut-out 43 for guiding the pivot movement and a pin 44 of the second part 42 of the analysis element 39 is guided in said arcuate cut-out. The analysis element 39 can be pivoted so far until its main direction of extent 47 is aligned perpendicular to the axial direction 18. An indication position of the analysis element 39 is thus reached which is shown in FIG. 2.

The second part 42 of the analysis element 39 has two punches 45, 46 which are oriented in the direction of the film 29 of the preparation element 20. The punches 45, 46 are configured such that they pierce the film 29 on the pivoting of the analysis element 39 into the indication position and thus open the preparation chambers 36, 37 of the preparation element 20 in the direction of the analysis element 39.

A sample collector 48 which has a handle 49, a shaft 50 and a receiving tip 51 is inserted into the inlet element 15 in the starting state shown in FIG. 1. The sample collector 48 is in this respect inserted so far into an envelope 52 that only a part of the handle 49 projects out of the envelope 52. The envelope 52 has a predominantly cylindrical outer contour and is dimensioned such that it sealingly terminates the inlet element 15 in the axial direction 18. The shaft 50 of the sample collector 48 moreover has a sealing disk 53 which has approximately the same outer contour as the envelope 52. It serves for closing the inlet element 15 when the sample collector 48 is inserted without an envelope 52 as shown in FIG. 2. The inlet chamber 54 in this case also serves as a storage space for the sample collector 48.

For analyzing a sample substance, for example in the form of saliva of a test person, starting from the starting state of the apparatus 10 in FIG. 1, the sample collector 48, including the envelope 52, is first removed from the inlet element 15. Subsequently, the sample substance is taken up by the receiving tip 51 of the sample collector 48 and the sample collector 48 is inserted into the receiving element 15 without an envelope 52. The receiving tip 51 thus dips into a washing-out liquid located in the inlet chamber 54. The received sample substance is washed out by shaking the apparatus 10. The mixture of sample substance and washing-out liquid produces a test liquid which can subsequently be analyzed.

It is also possible that first only the sample collector 48 is removed from the envelope 52 and the envelope 52 still closes the inlet element 15. The envelope 52 is then only removed after taking up the test substance.

After the washing out of the test substance, a respective defined quantity of test liquid is brought out of the inlet chamber 54 into the two preparation chambers 36, 37. For this purpose, the actuation element 19, and thus the inlet element 15, is rotated by 180% with respect to the cylindrical section 12 of the housing 11 and the inlet element 15 is thus displaced in the axial direction 18. The rotation and the axial displacement are ended when the connection collar 23 of the preparation element 20 abuts the abutment 38 of the cylindrical section 12 of the housing 11. The volumes of the preparation chambers 36, 37 thus increase by a respective defined degree. A vacuum respectively arises in the preparation chambers 36, 37 by this volume increase and test liquid is sucked in from the inlet chamber 54 on the basis of this vacuum. In this respect, exactly so much test liquid is respectively sucked in as the volumes of the preparation chambers 36, 37 are increased. The preparation position of the inlet element 15, and thus also of the preparation element 20, reached after the described rotation is shown in FIG. 2.

So that test liquid can be brought from the inlet chamber 54 into the preparation chambers 36, 37, the inlet chamber 54, and thus the inlet element 15, has two passages 56, 57 in the direction of the preparation chambers 36, 37, with only the passage 56 being able to be seen in FIG. 1 and only the passage 57 in FIG. 2. In the starting position shown in FIG. 1 and in the preparation position of the inlet element 15 shown in FIG. 2, the passages 56, 57 are not flush with the arcuate inflows 32, 33 of the holes 30, 31 of the center parts 21, 22 of the preparation element 20. The inlet chamber 54 is thus separate from the preparation chambers 36, 37 in these positions and no test liquid can flow from the inlet chamber 54 into the preparation chambers 36, 37. During the rotation of the inlet element 15 from the starting position into the preparation position, the passages 56, 47 are flush with the arcuate inflows 32, 33 of the holes 30, 31 of the center parts 21, 22 of the preparation element 20 so that then there is a connection between the inlet chamber 54 and the preparation chambers 36, 37 and test liquid can be sucked into the preparation chambers 36, 37 from the inlet chamber 54.

A respective reaction partner, for example in the form of gold conjugate, is present in the preparation chambers and prepares the test liquid. The preparation takes a fixed period of time of, for example, 4 minutes which have to be waited for.

After the end of the preparation, the prepared test liquid has to be brought from the preparation chambers 36, 37 onto an end of the test strips of the analysis element 29. For this purpose, the analysis element 39 is pivoted out of its position of rest shown in FIG. 1 into the indication position shown in FIG. 2 in which the main direction of extent 47 of the analysis element 39 has an angle of 90° with respect to the axial direction 18.

During the pivoting of the analysis element 39, punches 45, 46 pierce the film 29 which close the preparation chambers 36, 37 in the direction of the analysis element 39. As soon as the film 29 has been pierced, prepared test liquid can move from the preparation chambers 36, 37 onto an end of the test strips of the analysis element 39. The test liquid then flows through the test strips as described above so that the analysis results can be read off at the test strips after a fixed waiting time of, for example, 8 minutes.

Figure 4:
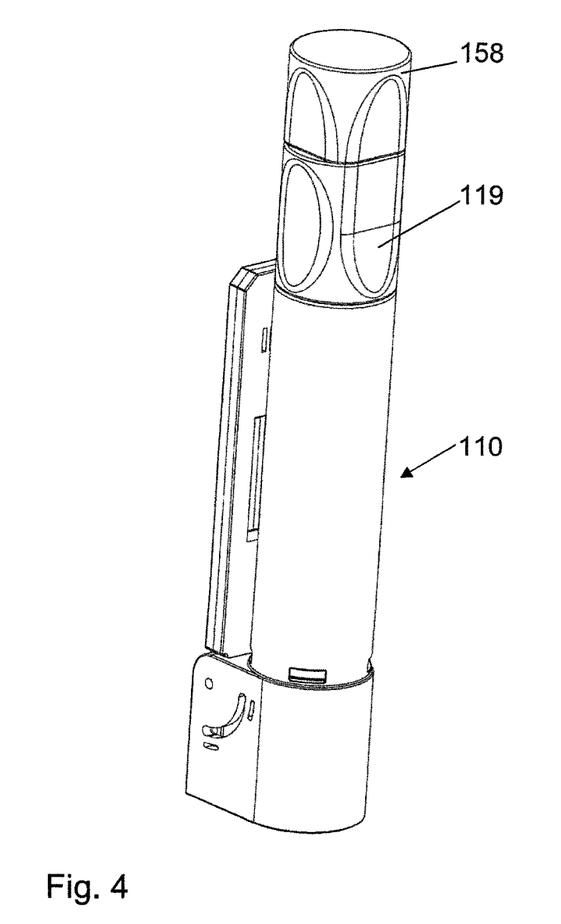
FIG. 4 is an alternative embodiment of an apparatus for analyzing a test liquid in a starting state.

In accordance with FIG. 4, an alternative apparatus 110 for analyzing a test liquid can have a removable plug 158 which can be plugged into the inlet element, not visible in FIG. 4, and thus adjoins an actuation element 119. The remaining design and the function of the apparatus are identical to those of the apparatus 10 of FIGS. 1 and 2.

Figure 5:
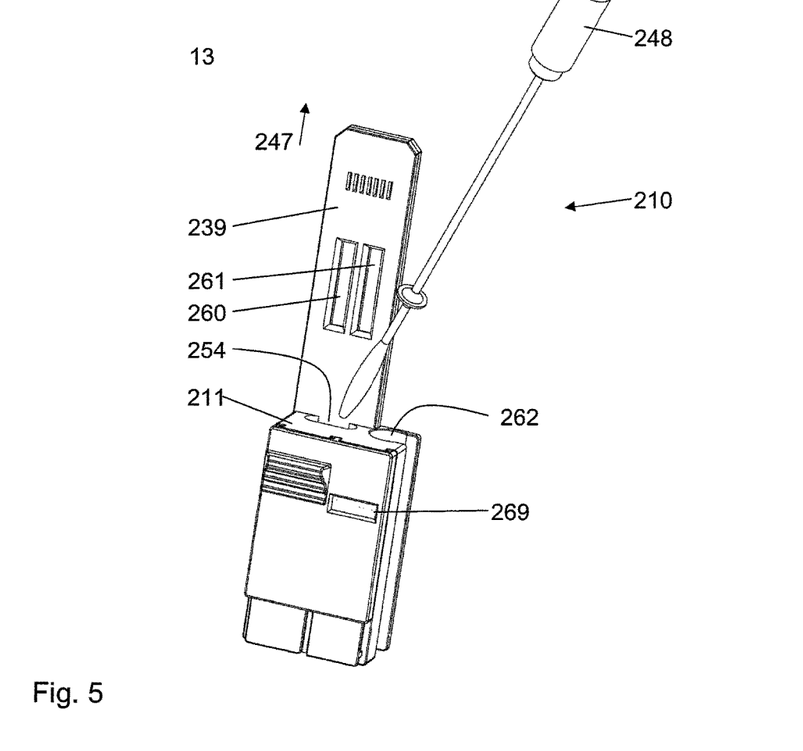
FIG. 5 is a further alternative embodiment of an apparatus for analyzing a test liquid in an analysis position.

In accordance with FIG. 5, a further alternative apparatus 210 for analyzing a test liquid has a housing 211 which is connected to an analysis element 239 The analysis element 239 has two test strips which are not shown in any more detail and which are partly visible via two cut-outs 260, 261 of the analysis element 239. The apparatus 210 likewise has a sample collector 248 which has an identical design to the sample collector 48 of FIG. 1. The apparatus 210 has a storage space 262 which is aligned in parallel with a main direction of extent 247 of the analysis element 239 and into which the sample collector 248 can be inserted, including an envelope 252, as shown only in FIG. 6. The housing 211 has an inlet chamber 254 which contains washing-out liquid, not shown further, and into which the sample collector 248 can be inserted and can be washed out as already described.

Figure 6:
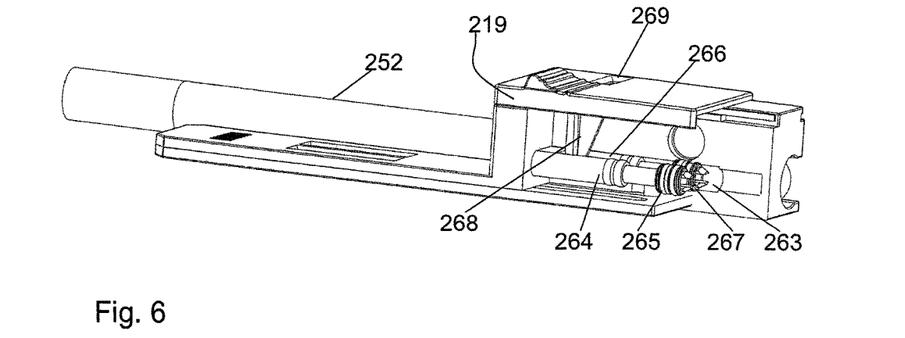
FIG. 6 is the apparatus of FIG. 5 in a starting position with partly cut-away details.

As shown in FIG. 6, the housing 211 has a first cylindrical inner housing space 263 and a second, further cylindrical inner housing space , not shown, in which two plungers 264, 266 and two ring pistons 265, 267 are arranged. The inner housing space 263 is in this respect aligned in parallel with the main direction of extent 247 of the analysis element 239. The function of the plungers 264, 266 and of the ring pistons 265, 267 will be explained in more detail in connection with FIGS. 7, 8 and 9. The plungers 264, 266 can adopt a starting position, a preparation position and an analysis position. To displace the plungers 264, 266, the plungers 264, 266 are coupled via a driver 268 with an actuation element 219 which can be displaced with respect to the housing 211 in the main direction of extent 247 of the analysis element 239. The actuation element 219 has a cut-out 269 through which markings, not shown, on the housing 211 are visible which indicate the current position of the plungers 264, 266. The indication of the position can also consist of the duration of a waiting time as already described above being indicated which is required at the current position of the plungers.

The function of the apparatus 210 will be explained in more detail in the following with respect to the schematic drawings in FIGS. 7, 8 and 9 which show a section through the plunger 264 and the ring piston 265 in the axial direction of the inner housing space 263. The function of the plunger 266 and of the ring piston 267 is identical.

The inlet chamber 254 is connected via an inflow line 270 to the inner housing space 263. In addition, an outflow line 271 leads from the inner housing space 263 to the analysis element 239.

The plunger 264 has a first section 276 which only has a minimally smaller diameter than the inner housing space 263. A second section 272 adjoins this first section 276; it has a smaller diameter and is ended by a driver 273 which in turn has a somewhat larger diameter. The transition from the first section 276 to the second section 272 in this respect takes place at a step 274 which has an end face 275 oriented in the direction of the driver 273. The ring piston 265 is arranged on the second section 272 of the plunger 264 and can thus be displaced between the step 274 and the driver 273 on the plunger 264.

Figure 7:
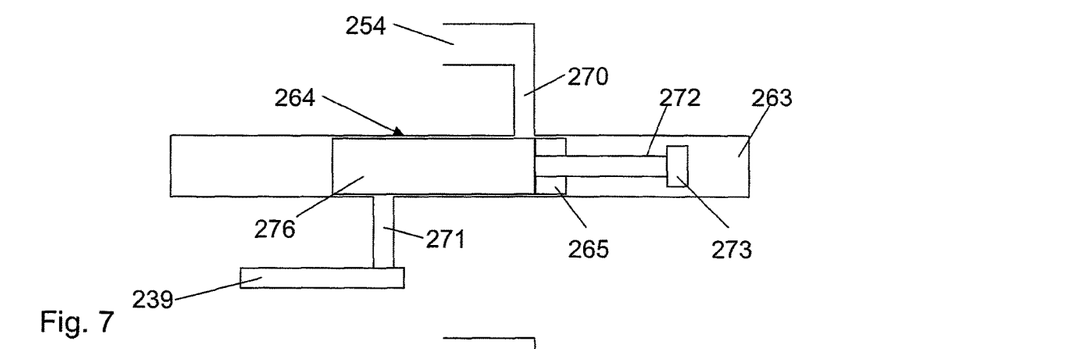
FIG. 7 is a schematic diagram of individual parts of the apparatus of FIG. 5 in a starting position.

In the starting position of the plunger 264 shown in FIG. 7, the plunger 264 is positioned so that the first section 76 of the plunger 264 closes both the inflow line 270 and the outflow line 271. No test liquid can thus flow from the inlet chamber 254 in the direction of the inner housing space 263. The plunger 264 is located in this position in the starting state of the apparatus 210 and during the washing out of the sample collector 248. The plunger can have one or more sealing lips or sealing elements, not shown, for a better sealing.

Figure 8:
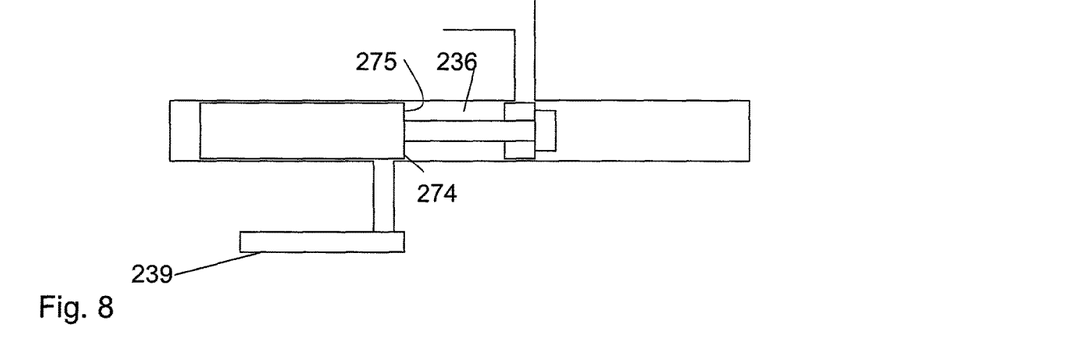
FIG. 8 is the individual parts of FIG. 7 in a preparation position.
Figure 9:
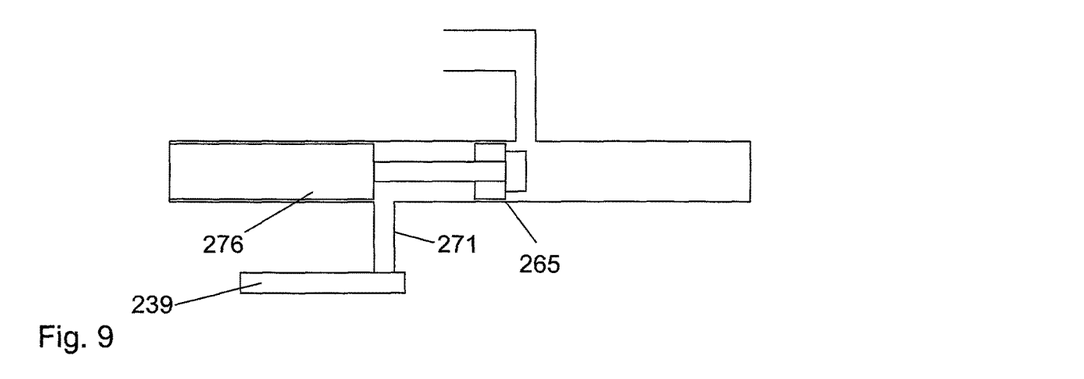
FIG. 9 is the individual parts of FIGS. 7 and 8 in the analysis position.

If test liquid should now be sucked out of the inlet chamber 264, the plunger 264 is displaced up to and into a preparation position shown in FIG. 8 by means of the actuation element 219 not shown in FIGS. 7, 8 and 9. On this displacement, the ring piston 265 which is displaceably arranged on the plunger 264, first remains stationary so that a preparation chamber 236 whose volume is increased during the displacement is formed between the end surface 275 of the named step 274 of the plunger 264 facing the driver 273 and thus also the ring piston 265 and the ring piston 265 in the inner housing space 263. The ring piston 265 remains stationary for so long until it is reached by the driver 273 and is subsequently taken along. From this point in time onward, the volume of the preparation chamber 236 remains unchanged. The preparation position is reached when the ring piston 265 closes the inflow line 270. To ensure an exact setting of the preparation position, a latching, not shown, is provided between the housing 211 and t actuation element 219; it fixes the actuation element 219 and thus the plunger 264 in individual positions, but can also be overcome by pressing. The ring piston can have one or more sealing lips or sealing elements, not shown, for a better sealing. The named latching can also be arranged within the inner housing space.

The volume of the preparation chamber 236 is increased by a defined degree by the displacement of the plunger 264 from the starting position into the preparation position. A vacuum thereby arises in the preparation chamber 236 so that a defined quantity of test liquid is sucked out of the inlet chamber 254 via this inflow line 270. It is prepared there as described.

After the end of the preparation, the prepared test liquid is conducted via the outflow line 271 to an end of the test strip, not shown in any more detail, of the analysis element 239. For this purpose, the plunger 264 and with it the ring piston 265 is displaced by means of the actuation element 219 starting from the preparation position into the analysis position. During this displacement, the first section 276 of the plunger 264 releases the outflow line 271 so that there is a connection between the preparation chamber 236 and the analysis element 239. The prepared test liquid can thus flow via the outflow line 271 to the analysis element 239 and thus through the test strip. It is also possible that the plunger 264 is displaced even further for setting the analysis position.

The invention claimed is:

1. An apparatus for analyzing a test liquid, comprising:
   an inlet chamber;
   a preparation chamber;
   an inlet element;
   an actuation element, the actuation element, the inlet chamber and the preparation chamber being arranged in an axial direction of the apparatus; and
   an analysis element,
   the inlet chamber being configured to receive the test liquid;
   the preparation chamber being arranged such that test liquid is capable of being brought from the inlet chamber via the preparation chamber onto the analysis element, and
   the preparation chamber being configured such that a volume thereof is variable,
   upon actuation of the actuation element, the inlet element is displaced in the axial direction such that the volume of the preparation chamber is increased, a vacuum is generated in the preparation chamber, causing a predetermined amount of the test liquid to be sucked out of the inlet chamber into the preparation chamber by the increase of the volume of the preparation chamber.

2. The apparatus in accordance with claim 1, wherein, in a starting state, the inlet chamber is configured to receive a washing-out liquid, resulting in the test liquid when mixed with a sample substance.

3. An apparatus for analyzing a test liquid, comprising:
   a housing having an inner housing space;
   an analysis element;
   an inlet chamber configured to receive the test liquid;
   an actuation element;
   an inlet element at least partly bounding the inlet chamber and being arranged at least partly within the inner housing space;
   a preparation chamber having a variable volume, the actuation element, the inlet chamber and the preparation chamber being arranged in an axial direction of the apparatus, and the preparation chamber being arranged such that test liquid is capable of being brought from the inlet chamber via the preparation chamber onto the analysis element, upon actuation of the actuation element, the inlet element is displaced in the axial direction such that the volume of the preparation chamber is increased, a vacuum is generated in the preparation chamber, causing a predetermined amount of the test liquid to be sucked out of the inlet chamber into the preparation chamber by the increase of the volume of the preparation chamber; and a preparation element at least partly bounding the preparation chamber and being arranged at least partly within the inner housing space, the preparation element and the inlet element being arranged after one another in an axial direction and being connected to one another such that a displacement of the inlet element in the axial direction increases the volume of the preparation chamber.

4. An apparatus for analyzing a test liquid, comprising:
a housing having an inlet chamber, an inner housing space, an inflow line from the inlet chamber to the inner housing space and an outflow line from the inner housing space to the analysis element, the inlet chamber being configured to receive the test liquid;
a plunger displaceably arranged in the inner housing space and having a step;
a ring piston arranged displaceable at least piece-wise on the plunger;
an analysis element; and
a preparation chamber having a variable volume, being formed by an end face of the step of the plunger facing the ring piston, by the inner housing space and by the ring piston, and being arranged such that test liquid is capable of being brought from the inlet chamber via the preparation chamber onto the analysis element, while the volume of the preparation chamber is increased, a vacuum is generated in the preparation chamber, causing a predetermined amount of the test liquid to be sucked out of the inlet chamber into the preparation chamber by the increase of the volume of the preparation chamber,
the plunger and the ring piston being configured and arranged such that, on a displacement of the plunger from a starting position into a preparation position, the ring piston first remains stationary with respect to the inner housing space and thus the volume of the preparation chamber is increased.

5. The apparatus in accordance with claim 3, wherein the inlet element has an actuation element arranged outside the housing and is configured such that a force for displacing the inlet element is capable of being introduced via the actuation element.

6. The apparatus in accordance with claim 5, wherein the inlet element has a first thread and the housing has a corresponding second thread so that, on a rotation of the inlet element with respect to the housing, the inlet element is displaced in the axial direction with respect to the housing.

7. The apparatus in accordance with claim 3, wherein the inlet element is configured to be rotated from a starting position into a preparation position for increasing the volume of the preparation chamber with respect to the housing and there is only a connection between the inlet chamber and the preparation chamber between the starting position and the preparation position.

8. The apparatus in accordance with claim 3, wherein a film is arranged between the preparation chamber and the analysis element, with the film being capable of being pierced by a punch for starting the analysis of the test liquid.

9. The apparatus in accordance with claim 8, wherein
the analysis element includes the punch,
the analysis element is pivotably connected to the housing and is configured to adopt a position of rest and an indication position, and
the analysis element is configured and arranged such that, on a rotation with respect to the housing, the punch of the analysis element pierces the film arranged between the preparation chamber and the analysis element and the analysis of the test liquid is thus started.

10. The apparatus in accordance with claim 9, wherein the analysis element has a predominantly parallelepiped basic shape and a main direction of extent of the analysis element predominantly is arranged in parallel with the axial direction in the position of rest.

11. The apparatus in accordance with claim 4, wherein the plunger and the ring piston are configured and arranged such that, in the starting position, the inflow line from the inlet chamber to the inner housing space is closed or, in the preparation position, the outflow line from the inner housing space to the analysis element is closed.

12. The apparatus in accordance with claim 4, wherein the plunger has a driver configured so as to bound a relative movement between the plunger and the ring piston, and the plunger and the ring piston
are arranged in the preparation position such that the inflow line from the inlet chamber to the inner housing space is closed; or
are capable of adopting an analysis position in which the outflow line from the inner housing space to the analysis element is open and a connection from the inlet chamber to the preparation chamber is closed.

13. The apparatus in accordance with claim 4, further comprising an actuation element arranged displaceably with respect to the housing, coupled to the plunger and by which a force can be introduced to displace the plunger.

14. The apparatus in accordance with claim 3, wherein the actuation element has a cut-out through which markings are visible indicating a current position of the inlet element or of the plunger.

15. The apparatus in accordance with claim 3, wherein the housing has a storage space for a sample collector.

* * * * *